(12) United States Patent
Barron et al.

(10) Patent No.: US 8,673,842 B2
(45) Date of Patent: *Mar. 18, 2014

(54) POLYPEPTOID PULMONARY SURFACTANTS

(75) Inventors: Annelise E. Barron, Chicago, IL (US); Ronald N. Zuckermann, El Cerrito, CA (US); Cindy W. Wu, Evanston, IL (US)

(73) Assignees: Annelise E. Barron, Palo Alto, CA (US); Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/385,310

(22) Filed: Feb. 13, 2012

(65) Prior Publication Data
US 2012/0258918 A1 Oct. 11, 2012

Related U.S. Application Data

(63) Continuation of application No. 11/120,071, filed on May 2, 2005, now Pat. No. 8,114,830, which is a continuation of application No. 09/788,308, filed on Feb. 16, 2001, now Pat. No. 6,887,845.

(60) Provisional application No. 60/182,847, filed on Feb. 16, 2000.

(51) Int. Cl.
| *A61K 38/00* | (2006.01) |
| *C07K 5/00* | (2006.01) |
| *C07K 14/785* | (2006.01) |

(52) U.S. Cl.
USPC ............. 514/1.1; 514/15.5; 530/300; 930/20; 930/30; 930/320

(58) Field of Classification Search
None
See application file for complete search history.

(56) References Cited

U.S. PATENT DOCUMENTS

| 6,022,955 A | 2/2000 | Sarin et al. |
| 6,887,845 B2 | 5/2005 | Barron et al. |

FOREIGN PATENT DOCUMENTS

| AU | 2001238442 | 8/2001 |
| EP | 0458167 | 11/1991 |
| WO | 01/60837 | 8/2001 |

OTHER PUBLICATIONS

Nguyen, J.T., et al. 1998 Science 282: 2088-2092.
Hamy, F., et al. 1997 PNAS 94: 3548-3553.
Yuan et al. 1998 Proteins 30: 136-143.
Sergei et al. 2000 J Virol 74:5101-5107.
Ding, J; Takamoto, DY; Von Nahmen, A; Lipp, MM; Lee, KYC; Waring, AJ; and Zasadzinski, JA; Effects of Lung Surfactant Proteins, SP-B and SP-C, and Palmitic Acid on Monolayer Stability; Biophys J., May 2001, 2262-2272, vol. 80, No. 5.
Lipp, MM; Lee, KYC; Zasadzinski, JA; and Waring, AJ; Phase and Morphology Changes in Lipid Monolayers Induced by SP-B Protein and Its Amino-Terminal Peptide; Science, Aug. 30, 1996, 1196-1199, vol. 273.
Kirshenbaum, K; Barron, AE; Goldsmith, RA, Armand, P, Bradley, EK; Truong, KTV; Dill, KA; Cohen, FE; and Zuckermann, RN; Sequence-Specific Polypeptides: A Diverse Family of Heteropolymers with Stable Secondary Structure; Proc. Nat'l. Acad. Sci., Apr. 1998, 4303-4308, vol. 95.
Nilsson, G; Gustafsson, M; Vandenbussche, G; Veldhuizen, E; Griffiths, WJ; Sjovall, J;.Haagsman, HP; Ruysschaert, JM; Robertson, B; Curstedt, T; and Johnsson, J; Synthetic Peptide-Containing Surfactants Evaluation of Transmembrane Versus Amphipathic Helices and Surfactant Protein C Poly-Valyl to Poly-Leucyl Substitution; Eur. J. Biochem, 1998, 116-124, vol. 255.
Seurynck, SL; Patch, JA; and Barron, AE; Simple, Helical Peptoid Analogs of Lung Surfactant Protein B; Chemistry & amp; Biology, Jan. 2005, 77-88, vol. 12.
Waring, A; Taeusch, W; Bruni, R; Amirkhanian, J; Fan, B. Stevens; R; and Young, J; Synthetic Amphipathic Sequences of Surfactant Protein-B Mimic Several Physicochemical and in Vivo Properties of Native Pulmonary Surfactant Proteins; Sep.-Oct. 1989, 308-313, vol. 2, No. 5.
Wu, CW; Seurynck, SL; Lee; KYC; and Barron, AE; Helical Peptoid Mimics of Lung Surfactant Protein C; Chemistry % amp; Biology, Nov. 2003, 1057-1063, vol. 10.
Armand, P, Kirshenbaum, K; Goldsmith, RA; Farr-Jones, S; Barron, AE, Truong, KTV; Dill, KA; Mierke, DF; Cohen, FE; Zukermann, RN; and Bradley, EK; NMR Determination of the Major Solution Conformation of a Peptoid Pentamer with Chiral Side Chains; Proc. Nat'l. Acad. Sci. USA, Apr. 1998, 4309-4314, vol. 95.

*Primary Examiner* — Marsha Tsay

(74) *Attorney, Agent, or Firm* — Reinhart Boerner Van Deuren s.c.

(57) ABSTRACT

The present invention provides spreading agents based on sequence-specific oligomers comprising a peptoid, a peptide-peptoid chimera, a retropeptoid or a retro(peptoid-peptide) chimera, and methods for using the same, including for the treatment of respiratory distress of the lungs. The spreading agents are sequence-specific oligomers, including retrosequence-specific oligomers, based on a peptide backbone, that are designed as analogs of surfactant protein-B or surfactant protein-C.

16 Claims, 14 Drawing Sheets

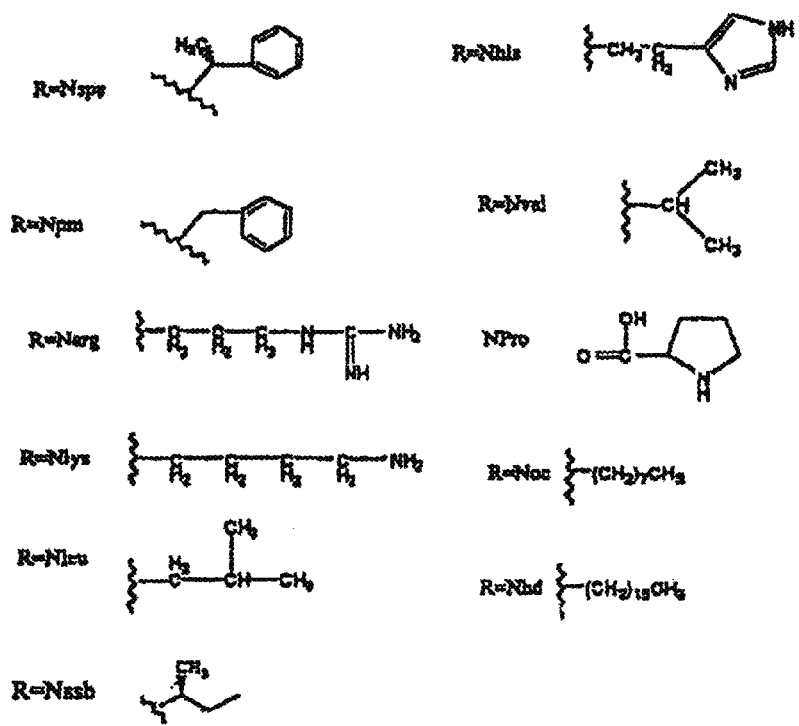

Fig. 7

SPCM1: H-NhdNhdProValHisLeuLysArg(NpmNspeNspe)₄Nspe₂-NH₂
SPCM2: H-NocNocProValHisLeuLysArg(NpmNspeNspe)₄Nspe₂-NH₂
SPCM3: H-PhePheProValHisLeuLysArg(NpmNspeNspe)₄Nspe₂-NH₂
Figure 7a:

SPCM4: H-NhdNhdProValHisLeuLysArg(Nssb)₁₄-NH₂
SPCM5: H-NocNocProValHisLeuLysArg(Nssb)₁₄-NH₂
SPCM6: H-PhePheProValHisLeuLysArg(Nssb)₁₄-NH₂
Figure 7b:

SPCM7: H-NocNocNProNValNHisNLeuNLysNArg(NpmNspeNspe)₄Nspe₂-NH₂
SPCM8: H-NpmNpmNProNValNHisNLeuNLysNArg(NpmNspeNspe)₄Nspe₂-NH₂
SPCM9: H-NocNocNProNValNHisNLeuNLysNArg(NpmNspeNspe)₄Nspe₂-NH₂
Figure 7c:

Fig. 10
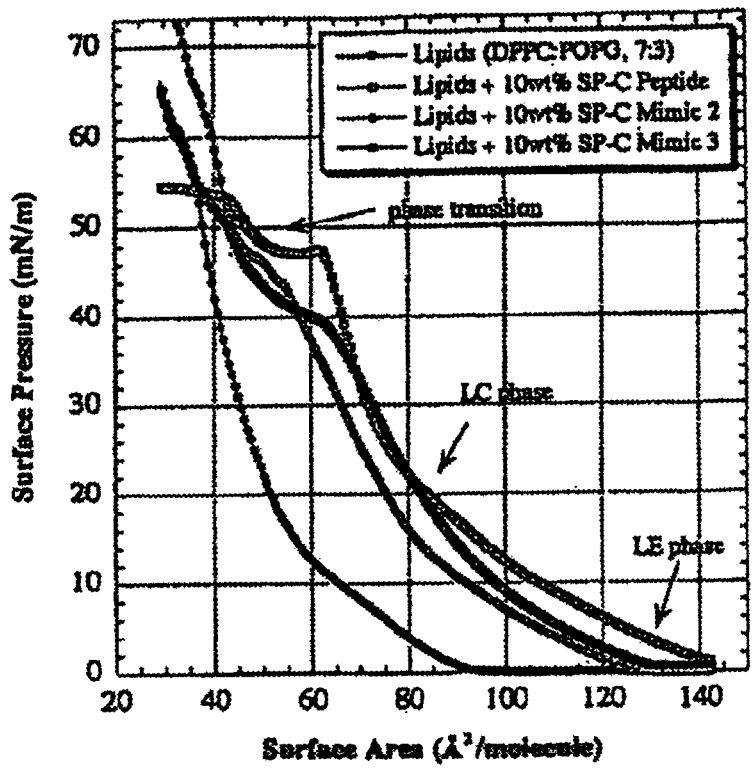
Figure 10A
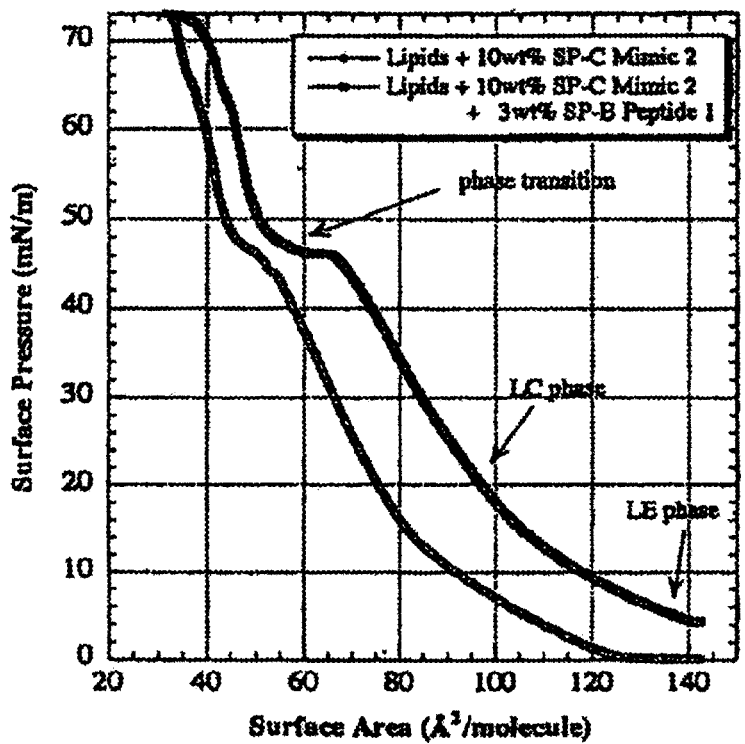
Figure 10B

POLYPEPTOID PULMONARY SURFACTANTS

This application is a continuation of and claims priority benefit from application Ser. No. 11/120,071 filed May 2, 2005, issued as U.S. Pat. No. 8,114,830 on Feb. 14, 2012, which was a continuation of application Ser. No. 09/788,308 filed Feb. 16, 2001, issued as U.S. Pat. No. 6,887,845 on May 3, 2005, and provisional patent application Ser. No. 60/182,847 filed Feb. 16, 2000, each of which is incorporated herein by reference in its entirety.

FIELD OF THE INVENTION

The present invention is directed to spreading agents based on sequence-specific oligomers comprising at least one N-substituted glycine (peptoid) residue, and methods for using the same, including for the treatment of respiratory distress of the lungs. The spreading agents are sequence-specific oligomers based on a peptide backbone, that are designed as analogs of surfactant protein-B or surfactant protein-C.

BACKGROUND OF THE INVENTION

"Pulmonary surfactant" or "lung surfactant" (LS) is a mixture of proteins and lipids that coats the internal surfaces of healthy mammalian lungs and enables normal breathing [1]. By virtue of its unique surface-active properties, lung surfactant markedly decreases the surface tension at the air-liquid interface of the myriad tiny air-sacs that perform gas exchange within the lung ("alveoli"), reducing the pressure required for alveolar expansion and decreasing the work of breathing [2, 3]. Lung surfactant also stabilizes the alveolar network upon exhalation, preventing collapse [3,4].

Natural lung surfactant is composed of 90-95% lipids and 5-10% protein [5, 6, 7]. Both protein and phospholipid fractions play critical roles in physiological surface activity [8]. Phosphatidylcholine (PC) variants are the most abundant components, making up 70-80% of the lipid fraction. 50-70% of the PC molecules are saturated and dipalmitoylated (DPPC). Anionic phosphatidylglycerol (PG) accounts for 8%, and other lipids as well as cholesterol are present in minor amounts [5].

In vitro and in vivo biophysical experiments have shown that the most critical lipid molecules for surface tension reduction are DPPC and PG [6, 7]. However, lipid mixtures alone are ineffective as lung surfactant replacements, because under physiological conditions and in the absence of "spreading agents," DPPC and PG do not adsorb to the air-liquid interface quickly, nor can they be respread rapidly as alveolar surface area changes cyclically [9]. Instead, a unique class of protein surfactants function as spreading agents.

Four surfactant-associated proteins are present with phospholipids on the alveolar hypophase: SP-A, SP-B, SP-C, and SP-D [10]. These fall into two major subgroups: hydrophilic surfactant proteins SP-A and SP-D, and hydrophobic surfactant proteins SP-B and SP-C. SP-A and SP-D control surfactant metabolism, and also play important immunological roles as a defense against inhaled pathogens [11]. But for therapeutic lung surfactant replacements, it is the biophysical properties of surfactant—as they affect the mechanical properties of the lung—that are important for the treatment of respiratory distress. Neither SP-A nor SP-D is responsible for the surface tension-lowering properties of surfactant [6], so they are typically omitted from surfactant replacements.

Surfactant-associated proteins are required for proper functioning of lung surfactant [8], and it is the small hydrophobic proteins SP-B and SP-C that enable low surface tensions on the alveolar hypophase, endowing a proper dynamic behavior of lipid monolayers [12-14]. SP-B and SP-C interact non-synergistically with lipids to enable easy breathing [15]. In vivo rescue experiments with premature rabbits [16], in vivo blocking of SP-B with monoclonal antibodies [17], and studies with genetically-engineered SP-B-deficient mice [18] all confirm the necessity of SP-B and SP-C proteins for functioning of lung surfactant in vivo [8]. Both facilitate rapid adsorption of phospholipids to an air/water interface, allowing rapid re-spreading of phospholipids as alveoli expand and contract. Both influence the monolayer's phase behavior, and reduce surface tension on alveoli at expiration to <1 mN/m [14, 19].

Neonatal Respiratory Distress Syndrome (NRDS) is a leading cause of infant mortality in the United States [6]. In the absence or dysfunction of pulmonary surfactant, mammalian lungs are incompliant and vulnerable to alveolar collapse upon expiration, due to excessive surface tension forces. Preterm infants who have gestated <29 weeks have not yet begun to secrete lung surfactant into alveolar spaces [20] and suffocate after delivery without surfactant replacement therapy. Hence, it is standard care for infants with NRDS (given prophylactically for infants born before 28 weeks gestation), and is expected to gain clinical significance for "acute RDS" (ARDS) in adults and children [6].

Adults and children would also benefit from an effective, non-immunogenic, bioavailable, and less expensive synthetic surfactant replacement. Dysfunction of surfactant is a major contributor to the lethal ARDS, which can occur in adults and children after shock, bacterial sepsis, hyperoxia, near drowning, or aspiration [6]. ARDS is a leading cause of death in intensive care units, and as yet has no generally effective, economically viable treatment [7]. The dysfunction of lung surfactant in adults and children most typically results from the encroachment of blood serum or other foreign fluids into the lungs. Serum proteins disrupt and inhibit the spreading of natural surfactant by poorly-understood biorecognition and bioaggregation mechanisms [9, 21]. Lung surfactant replacement therapy was investigated for the treatment of adult and child ARDS [22-25]. But the large doses necessary for adults make this potentially useful treatment far too expensive [26].

Academic and industrial research have resulted in the commercialization of several functional lung surfactant replacements, but the material is quite expensive ($1000 per 1.2-mL dose) and different formulations give highly variable results [27, 28]. Animal-derived surfactants are most expensive, and work best to restore lung function quickly, but raise purity and immunological concerns [27]. If infants with NRDS survive surfactant replacement therapy (they need up to four doses every 6-8 hours after birth), they begin to secrete their own pulmonary surfactant within 96 hours [5].

Currently, the two classes of lung surfactant replacements commercially available for the treatment of respiratory distress syndrome (RDS) are "natural" and "synthetic." "Natural surfactant replacements" are prepared from animal lungs by lavage or extraction with organic solvents, and purified by chromatography [5, 6, 26]. A number of animal-derived surfactant replacements are FDA-approved [29-32]. "Synthetic surfactant replacements" are by definition protein-free, and are made from synthetic phospholipids with added chemical agents (lipids or detergents) to facilitate adsorption and spreading [33, 34]. These protein-free synthetic formulations do not work well, and have fallen out of common use.

A third, not-yet-commercially-available class of formulations is the "biomimetic lung surfactants." Biomimetic surfactants are designed to mimic the biophysical characteristics of natural lung surfactant while not sharing its precise molecular composition. These formulations contain synthetic phospholipid mixtures in combination with recombinantly-derived or chemically-synthesized peptide analogs to SP-B and/or SP-C [7].

Since biomimetic surfactant formulations are not available, doctors must choose between animal-derived or synthetic surfactant replacements [27, 35, 36]. Despite worries about the possible contamination of animal-derived surfactants with animal viruses, and problems with rapid surfactant biodegradation resulting in a need for multiple doses [27], most doctors favor animal-derived formulations [6]. Current synthetic formulations (although safer, generally effective, and less expensive than natural surfactants) [27] have inferior in vivo efficacy (saving 1 fewer infant per 42 treated [27, 36]), primarily because better analogs for the SP-B and SP-C proteins are needed.

Bovine and porcine SP are ~80% homologous to human SP, and are recognized as foreign by the immune system even in some infants [17, 37, 38]. Antibodies that develop to these homologous SP sequences have the potential to inactivate natural human SP and lead to respiratory failure. This has not yet been found to occur in newborns [5, 6], but for adults with ARDS, auto-antibodies could be a serious problem [27]. Surfactant replacement therapy in premature infants has a high failure rate (~65% of infants die or develop chronic lung disease (bronchopulmonary dysplasia, BPD) after therapy) [27].

When human medicines are extracted from animals it is impossible to eliminate the chance of cross-species transfer of antigenic or infectious agents or unforeseeable biological contamination [39]. Synthetic, biomimetic surfactants obviate these risks, and may also offer greater bioavailability (fewer doses, hence lower cost) and less liability to inhibition. Synthetic surfactants must be improved until efficacy for RDS rescue therapy with synthetics matches that of natural surfactant.

To obviate the need for animal-derived medicines, several groups have undertaken de novo chemical synthesis of truncated peptide mimics of SP-B and SP-C for surfactant preparations [7]. The majority of these synthetic, biomimetic polypeptides have been biophysically functional in vitro and in vivo (i.e., they have been successful to some degree in promoting achievement of low surface tensions and facilitating rapid re-spreading of surfactant lipids, allowing the rescue of premature animals with RDS). Several workers, including Kang [40], Bruni [41], and Lipp [42-44], have made and tested SP-B fragments. All succeeded in making biophysically-active SP-B analogs. Interestingly, a 25-residue peptide from the amino-terminus of SP-B seems to capture the surface-active properties of full-length SP-B [42]. Fujiwara [45] and Notter [46] made shortened mimics of SP-C, while Wang [46] made full-length, palmitoylated SP-C peptide and reported that acylation of cysteines is critical for SP-C's biophysical function. Takei et al. [45] omitted the palmitoyl groups and found that shortened SP-C peptide mimics (residues 5-32) retain "full biophysical activity" in vitro and in vivo. What is striking about these studies is that many groups have made peptide mimics of SP, and all were successful to some degree. This provides strong evidence of the tolerance of this system for slight variations in SP analogs—to be expected since they interact primarily with lipids, which is likely an interaction of a much less specific nature than many biomolecule interactions.

As indicated by the notations herein, these and other aspects of the prior art as related to an understanding of this invention can be found in the following:

1. Pattle, R. E., Properties, function, and origin of the alveolar lining layer. Nature, 1955, 175: p. 1125-1126.
2. Clements, J. A., Surface tension of lung extracts. Proc. Soc. Exp. Biol. Med., 1957. 95: p. 170-172.
3. Clements, J. A., E. S. Brown, and R. P. Johnson, Pulmonary surface tension and the mucus lining of the lungs: Some theoretical considerations. J. Appl. Physiol., 1958. 12: p. 262-268.
4. Putz, G., et al., Comparison of captive and pulsating bubble surfactometers with use of lung surfactants. J. Appl. Physiol., 1994. 76: p. 1425-1431.
5. Creuwels, L. A. J. M., M. G. van Golde, and H. P. Haagsman, The pulmonary surfactant system: Biochemical and clinical aspects. Lung, 1997. 175: p. 1-39.
6. Notter, R. H., and Z. Wang, Pulmonary surfactant: Physical chemistry, physiology, and replacement. Reviews in Chemical Engineering, 1997. 13: p. 1-118.
7. McLean, L. R., and J. E. Lewis, Biomimetic pulmonary surfactants. Life Sciences, 1995. 56: p. 363-378.
8. King, R. J., and J. A. Clements, Surface active materials from dog lung. II. Composition and physiological correlations. Am. J. Physiol., 1972. 223: p. 715-726.
9. Cockshutt, A., D, Absolom, and F. Possmayer, The role of palmitic acid in pulmonary surfactant: Enhancement of surface activity and prevention of inhibition by blook proteins. Biochim, Biophys. Acta, 1991. 1085: p. 248-256.
10. Johansson, J., T. Curstedt, and B. Robertson, The proteins of the surfactant system. Eur. Respir. J., 1994. 7: p. 372-391.
11. Khoor, A., et al., Developmental expression of SP-A and SP-A mRNA in the proximal and distal epithelium in the human fetus and newborn. J. Histochem. Cytochem, 1993. 41: p. 1311-1319.
12. Hall, S. B., et al., Importance of hydrophobic apoproteins as constituents of clinical exogenous surfactants. Am. Rev. Respiratory Disorders, 1992. 145: p. 24-30.
13. Goerke, J., Pulmonary surfactants-Physicochemical aspects. Current Opinion in Colloid & Interface Science, 1997. 2: p. 526-530.
14. Wang, Z., S. B. Hall, and R. H. Notter, Roles of different hydrophobic constituents in the adsorption of pulmonary surfactant. Journal of Lipid Research, 1996. 37: p. 790-798.
15. Wang, Z., et al., Differential activity and lack of synergy of lung surfactant proteins SP-B and SP-C interactions. Journal of Lipid Research, 1996. 37: p. 1749-1760.
16. Rider, E. D., et al., Treatment responses to surfactants containing natural surfactant proteins in preterm rabbits. Am. Rev. Respir. Dis., 1993. 147: p. 669-676.
17. Robertson, B., et al., Experimental neonatal respiratory failure induced by a monoclonal antibody to the hydrophobic surfactant-associated protein SP-B. Pediatr. Res., 1991. 30: p. 239-243.
18. Tokeida, K., et al., Pulmonary dysfunction in neonatal SP-B-deficient mice. Am. J. Physiol., 1997. 273: p. L875-L882.
19. Taneva, S. and K. M. W. Keogh, Pulmonary surfactant proteins SP-B and SP-C in spread monolayers at the air-water interface. III. Proteins SP-B plus SP-C with phospholipids in spread monolayers. Biophys. J., 1994. 66: p. 1158-1166.
20. Goerke, J. and J. A. Clements, Alveolar surface tension and lung surfactant, in Handbook of Physiology: The Respiratory System—Control of Breathing. 1986, American Physiology Society: Bethesda, Md. p. 247-261.

21. Jobe, A., et al, Permeability of premature lamb lungs to protein and the effect of surfactant on that permeability. J. Appl. Physiol., 1983. 55: p. 169-176.
22. Gregory, T. J., et al., Survanta supplementation in patients with acute respiratory distress syndrome (ARDS). Am. J. Resp. Cell. Mol. Bio., 1994. 149: p. A567.
23. Spragg, R. G., et al., Acute effects of a single dose of porcine surfactant on patients with adult respiratory distress syndrome. Chest, 1994. 105: p. 195-202.
24. Hafner, D., et al., Dose response comparisons five lung surfactant factor (LSF) preparations in an animal model of adult respiratory distress syndrome (ARDS). Br. J. Pharmacol., 1995. 116: p. 451-458.
25. Willson, D. F., et al., Calf's lung surfactant extract in acute hypoxemic respiratory failure in children. Crit. Care Med., 1996. 24: p. 1316-1322.
26. Kattwinkel, J., Surfactant: Evolving issues. Clinics in Perinatology, 1998. 25: p. 17-32.
27. Whitelaw, A., Controversies: Synthetic or natural surfactant treatment for respiratory distress syndrome? The case for synthetic surfactant. J. Perinat. Med., 1996. 24: p. 427-435.
28. Halliday, H. L., Synthetic or natural surfactants. Acta Paediatr., 1997. 86: p. 233-7.
29. Hoekstra, R. E., et al., Improved neonatal survival following multiple doses of bovine surfactant in very premature neonates at risk of respiratory distress syndrome. Pediatrics, 1991. 88: p. 19-28.
30. Gortner, L. A., A multicenter randomized controlled trial of bovine surfactant for prevention of respiratory distress syndrome. Lung, 1990. 168 (Suppl): p. 864-869.
31. Kendig, J. W., et al., A comparison of surfactant as immediate prophylaxis and as rescue therapy in newborns of less than 30 weeks gestation. N. Engl. J. Med., 1991. 324: p. 865-871.
32. Collaborative European Multicenter Study Group. Surfactant replacement therapy in severe neonatal respiratory distress syndrome: An international randomized clinical trial. Pediatrics, 1988. 82: p. 683-691.
33. Morley, C. J., et al., Dry artificial lung surfactant and its effect on very premature babies. Lancet, 1981. i: p. 64-68.
34. Phibbs, R. H., et al., Initial clinical trial of Exosurf, a protein-free synthetic surfactant, for the prophylaxis and early treatment of hyaline membrane disease. Pediatrics, 1991. 88: p. 1-9.
35. Zetterström, R., Surfactant therapy: Clinical implications. Acta Paediatr., 1996. 85: p. 641-641.
36. Halliday, H. L., Controversies: Synthetic or natural surfactant. The case for natural surfactant. J. Perinat. Med., 1996. 24: p. 417-426.
37. Strayer, D. S., et al., Surfactant anti-surfactant immune complexes in infants with respiratory distress syndrome. Am. J. Pathology, 1986. 122: p. 353-362.
Chida, S., et al., Surfactant proteins and anti-surfactant antibodies in sera from infants with respiratory distress syndrome. Pediatrics, 1991. 88: p. 84-89.
39. Long, W., Synthetic surfactant. Seminars in Perinatology, 1993. 17: p. 275-284.
40. Kang, J. H., et al., The relationships between biophysical activity and the secondary structure of synthetic peptides from the pulmonary surfactant protein SP-B. Biochem. and Molec. Biol, Intl., 1996. 40: p. 617-627.
41. Bruni, R., H. W. Taeusch, and A. J. Waring, Surfactant Protein B: Lipid interactions of synthetic peptides representing the amino-terminal amphipathic domain. Proc. Natl. Acad. Sci. USA, 1991. 88: p. 7451-7455.
42. Lipp, M. M., et al., Phase and morphology changes in lipid monolayers induced by SP-B protein and its amino-terminal peptide. Science, 1996. 273: p. 1196-1199.
43. Lipp, M. M., et al., Fluorescence, polarized fluorescence, and Brewster angle microscopy of palmitic acid and lung surfactant protein B monolayers. Biophys. J., 1997. 72: p. 2783-2804.
44. Nag, K., et al., Phase transitions in films of lung surfactant at the air-water interface. Biophys. J., 1998. 74: p. 2983-2995.
45. Takei, T., et al., The surface properties of chemically synthesized peptides analogous to human pulmonary surfactant protein SP-C. Biol. Pharm. Bull., 1996. 19: p. 1247-1253.
46. Wang, Z., et al., Acylation of pulmonary surfactant protein-C is required for its optimal surface active interactions with phospholipids. J. Biol. Chem., 1996. 271: p. 19104-19109.
47. Simon, R. J., et al., Peptoids: A modular approach to drug discovery. Proc. Natl. Acad. Sci. USA, 1992. 89: p. 9367-9371.
48. Zuckermann, R. N., et al., Efficient method for the preparation of peptoids [oligo (N-substituted glycines)] by sub-monomer solid phase synthesis. J. Am. Chem. Soc., 1992. 114: p. 10646-10647.
49. Kruijtzer, J. a. L., R., Synthesis in Solution of Peptoids using Fmoc-protected N-substituted Glycines. Tetrahedron Letters, 1995. 36(38): p. 6969-72.
50. Miller, S. M., et al., Comparison of the proteolytic susceptibilities of homologous L-amino acid, D-amino acid, and N-substituted glycine peptide and peptoid oligomers. Drug Development Research, 1995. 35: p. 20-32.
51. Borman, S., Peptoids eyed for gene therapy applications. C & E News, 1998. 76: p. 56-57.
52. Kirshenbaum, K., et al., Sequence-specific polypeptoids: A diverse family of heteropolymers with stable secondary structure. Proc. Natl. Acad. Sci., U.S.A., 1998. 95: p. 4303-4308.
53. Figliozzi, G. M., et al., Synthesis of N-substituted glycine peptoid libraries. Meth. Enzymology, 1996. 267: p. 437-447.
54. Curstedt, T., et al. Low molecular mass surfactant protein type I: The primary structure of a hydrophobic 8-kDa polypeptide with 8 half cystine residues. Eur. J. Biochem., 1988. 172: p. 521-525.
55. Johansson, J., T. Curstedt, and H. Jörnvall, Surfactant protein B: Disulfide bridges, structural properties, and kringle similarities. Biochemistry, 1991, 30: p. 6917-6921.
56. Johansson, J., H. Mrnvall, and T. Curstedt, Human surfactant polypeptide SP-B disulfide bridges, C-terminal end, and peptide analysis of the airway form. FEBS Lett., 1992. 301: p. 165-167.
57. Cochrane, C. G. and S. D. Revak, Pulmonary surfactant protein B (SP-B): Structure-function relationships. Science, 1991. 254: p. 566-568.
58. Van den Bussche, G., et al., Secondary structure and orientation of the surfactant protein SP-B in a lipid environment: A FTIR spectroscopy study. Biochemistry, 1992. 31: p. 9169-9176.
59. Pérez-Gil, J., A. Cruz, and C. Casals, Solubility of hydrophobic surfactant proteins in organic solvent/water mixtures: Structural studies on SP-B and SP-C in aqueous organic solvents and lipids. Biochim. Biophys. Acta, 1993. 1168: p. 261-270.

60. Johannson, J., et al., The NMR structure of the pulmonary surfactant-associated polypeptide SP-C in an apolar solvent contains a valyl-rich α-helix. Biochemistry, 1994. 33: p. 6015-6023.
61. Pastrana, B., A. J. Mautone, and R. Mendelsohn, FTIR studies of secondary structure and orientation of pulmonary surfactant SP-C and its effect on the dynamic surface properties of phospholipids. Biochemistry, 1991. 30: p. 10058-10064.
62. Shiffer, K., et al., Lung surfactant proteins SP-B and SP-C alter the thermodynamic properties of the phospholipid membrane: A differential calorimetry study. Biochemistry, 1993. 32: p. 590-597.
63. Morrow, M. R., et al., $^2$H-NMR studies of the effect of pulmonary surfactant SP-C on the 1,2-dipalmitoyl-sn-glycerol-3-phosphocholine headgroup: A model for trans-bilayer peptides in surfactant and biological membranes. Biochemistry, 1993. 32: p. 11338-11344.
64. Van den Bussche, G., et al., Structure and orientation of the surfactant-associated protein C in a lipid bilayer. Eur. J. Biochem., 1992. 203: p. 201-209.
65. Curstedt, T., et al., Hydrophobic surfactant-associated polypeptides: SP-C is a lipopeptide with two palmitoylated cysteine residues, whereas SP-B lacks covalently linked fatty acyl groups. Proc. Natl. Acad. Sci. USA, 1990. 87: p. 2985-2989.
66. Creuwels, L. A. J. M., et al., Neutralization of the positive charges of surfactant protein C: Effects on structure and function. J. Biol. Chem., 1995. 270: p. 16225-16229.
67. Johansson, J., Curstedt, T, Robertson, B, Synthetic protein analogues in artificial surfactants. Acta Paediatr, 1996. 85: p. 642-6.

SUMMARY OF THE INVENTION

The present invention provides a novel class of functional, biomimetic spreading agents based on non-natural, sequence-specific polymers, "polypeptoids," peptoid-peptide chimera, "retropolypeptoids" and retro(peptoid-peptide) chimera, as additives to exogenous lung surfactant preparations. As used herein, the terms "retropolypeptoid," "retropeptoid" or "retro(peptoid-peptide) chimera" refers to a compound whose sequence is the reverse of the natural protein, i.e., the amino-to-carboxy sequence of the compound is substantially equal to the carboxy-to-amino sequence of the peptide, such as surfactant proteins B and C. (See, FIG. 1, below.) The spreading agents are designed to mimic the surface-active properties of surfactant proteins B and C (SP-B and SP-C). The SP-mimics (SPM) are added to a lipid admixture to create a functional, biomimetic lung surfactant that is safe, reliable, bioavailable, cost-effective, and non-immunogenic.

In light of the foregoing, it is an object of the present invention to provide polypeptoid spreading agents and related pulmonary surfactant compositions and/or related methods for their preparation and/or use, thereby overcoming various deficiencies and shortcomings of the prior art, including those outlined above. It will be understood by those in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide peptoid spreading agents and/or compositions as replacements for naturally-occurring surfactant-associated proteins B and C, for reasons including resulting protease resistance and low immunogenicity.

It can also be an object of the present invention to provide one or more non-natural peptoid spreading agents for use in the preparation and/or administration of related pulmonary surfactant compositions.

It can also be an object of the present invention to provide a replacement for naturally-occurring surfactant-associated proteins, as well as those synthetic analogs, such replacements having enhanced bio availability and a resulting increased efficacy.

It can also be an object of the present invention to provide a replacement peptoid spreading agent and/or pulmonary surfactant composition having a monomeric, stable, helical structure, increased solubility and enhanced resistance to aggregation, such properties as heretofore unavailable through such agents and/or compositions of the prior art.

Other objects, features, benefits and advantages of the present invention will be apparent from this summary and its descriptions of various preferred embodiments, and will be readily apparent to those skilled in the art having knowledge of pulmonary surfactants and their preparational use. Such objects, features, benefits and advantages would be apparent from the above as taken into conjunction with the accompanying examples, data, figures and all reasonable inferences to be drawn therefrom, alone or in consideration with their advances over the prior art.

In part, the present invention is directed to a non-natural heteropolymeric pulmonary spreading agent including (1) at least one N-substituted glycine residue and (2) at least one amino acid residue corresponding to a natural surfactant-associated protein selected from the group consisting of surfactant-associated proteins B and C. As explained elsewhere herein, synthetic techniques well-known to those skilled in the art provide for N-substitution limited only by availability, stability and/or design of a suitable amine precursor for use in the associated synthesis. In preferred embodiments, the N-substituent is a moiety selected from the group consisting of the proteinogenic amino acid sidechains and/or carbon homologs thereof.

Regardless, with respect to the surfactant-associated protein, preferred spreading agents include amino acid residues corresponding to surfactant-associated protein B, in particular residues 1-25 thereof. Alternatively, preferred embodiments can otherwise include amino acid residues corresponding to surfactant-associated protein C, in particular residues 1-35 thereof. Such amino acid residues can be provided in a sequence corresponding to their presence in the natural protein or in such a way as to mimic the overall structural and/or hydrophotic or polar properties thereof.

In part, the present invention can also include a pulmonary surfactant composition, including (1) a non-natural spreading agent as described above and (2) a lipid component which, together with the spreading agent, provides a physiological alveolar surface activity. Such lipid components can include naturally-occurring phospholipids, non-natural analogs of said phospholipids, commercial surface-active agents and a combination thereof. In preferred embodiments, the lipid is an admixture of phospholipids of the type described elsewhere herein. Such preferred embodiments can also include a palmitic acid additive.

In part, the present invention can also include a method of using N-substitution to enhance conformational control of a surface-associated protein mimic compound. The method includes preparing a surfactant-associated protein mimic composition having at least one glycine residue, the preparation providing N-substitution of the glycine residue to an extent sufficient to enhance monomeric, helical confirmation of the protein mimic compound. Representative N-substitutions and the resulting helical conformation are as described in several examples, herein, and result in an increased solubility and, hence, utility of the resulting protein mimic compound.

In part, as also demonstrated herein, the present invention can also include a method for controlling alveolar surface activity. Such control is demonstrated by procedures and protocols accepted by those skilled in the art to demonstrate reduced alveolar surface tension. Such methods include (1) preparing a pulmonary surfactant composition including the non-natural heteropolymeric spreading agent having at least one N-substituted glycine residue, and a lipid admixture; and (2) administering the surfactant composition in an amount sufficient and conditions conducive to reduce alveolar surface tension. Such amounts and method parameters are as described elsewhere, herein, or would be understood to those skilled in the art and made aware of this invention.

In part, the present invention includes one or more pulmonary surfactant compositions, which together with a lipid admixture provide results commensurate with or exceeding those available through other embodiments of this invention. For instance, examples 7 and 8, below, provide two of several such spreading agents, structural alternatives to which can be represented by the following:

$HN\text{-}X_1X_2$(SEQ ID NO: 1)$(NX_3)_n\text{-}CONH_2$ and $HN\text{-}X_1X_2$ProNvalNpm/NleuNlysNarg$(NX_3)_n\text{-}CONH_2$.

Polypeptoids are (N-substituted glycine) polymers based on a polypeptide backbone and can be produced by an efficient, automated solid-phase synthesis that allows the incorporation of diverse N-pendant sidechains in a sequence-specific manner [47, 48]. The major advantage of using polypeptoids for biomedical applications is that despite their close similarity to polypeptides, these molecules are essentially invulnerable to protease degradation and hence are simultaneously more stable in vivo than polypeptides and less likely to be recognized by the immune system.

The use of peptoid-based analogs, i.e., peptide analogs, of the surfactant proteins has, among many other advantages, two major advantages: (1) It has enhanced bioavailability, thereby allowing lower doses and reducing the need for multiple doses, and (2) it is safer and less expensive than natural surfactants, which contain animal proteins.

One embodiment of the present invention provides a protein analog spreading agent having surface-active properties similar to those of surfactant protein-B and/or surfactant protein-C. As used herein, the term "protein analog" refers to a polypeptoid, a peptoid-peptide chimera, or a retropeptoid that contains at least one peptoid residue. That is, the side chains, i.e., $R_i$ of FIG. 1, are nearly identical in the peptoid to those of the corresponding peptide. However, since a peptoid and peptide have different points of side chain attachment, the side chain residue of peptoid, i.e., $R_i$ group, may contain up to 3, preferably up to 2, additional carbon atoms or may contain 2 or less, preferably 1 or less, fewer carbon atoms relative to the corresponding peptide side chain.

The surface-active properties of the protein analog spreading agent of the present invention include reducing the adsorption surface tension of air-water interface to less than about 30 mN/m within 20 minutes of adsorption. The surface-active properties of spreading agents of the present invention can also include reducing the surface tension upon compression of the film surface to less than about 15 mN/m on the first or second compression. The surface-active properties can further include producing enrichment of DPPC content of the film area during cycling of the film area. Appropriate tests for each of these surface-active properties can be found, for example, in the Examples section.

Another embodiment of the present invention provides a protein analog spreading agent of surface protein-B or surface protein-C, wherein the protein analog spreading agent comprises a peptoid analog segment sharing the sequence of residues 1-25, preferably 1-28, of surface protein-B or residues 2-32, preferably 1-35, of surface protein-C, and wherein the protein analog segment comprises at least one peptoid residue.

More preferably, the peptoid analog segment comprises at least about 25% peptoid residues. As used herein, reference to "sharing the sequence" of specified residues of surface protein-B or surface protein-C means a molecule having a sequence comprising at least 70% (more preferably 80%, 90% and 95%) of the specified residues in the order of or to mimic the specified residues in surface protein-B or surface protein-C, even though those 70%, or more in preferred embodiments, of the specified residues may be interspersed with other residues. Reference to a "surfactant protein-B" or "surfactant protein-C" refers to any naturally occurring sequence for a surfactant protein-B or surfactant protein-C, such as the known sequences for human surface protein-B or surface protein-C.

Yet another embodiment of the present invention provides a pulmonary surfactant composition comprising: (a) a protein analog spreading agent described above; and (b) a phospholipid admixture.

Still another embodiment of the present invention provides a method for treating respiratory distress syndrome comprising administering the pulmonary surfactant composition described above to a patient in need of the same. Preferably, a patient is an animal, more preferably a mammal, and most preferably human.

BRIEF DESCRIPTION OF THE DRAWINGS

FIG. 1 illustrates a comparison of the chemical structures of peptides, peptoids, and retropeptoids for trimers having arbitrary side-chains $R_i$;

FIG. 2 is a schematic illustration of the "sub-monomer," synthetic protocol for production of peptoid oligomers via a solid-phase synthesis. These two steps are simply repeated for the addition of each monomer unit. When the full polypeptoid has been synthesized, it is cleaved off the resin with trifluoroacetic acid and purified by reversed-phase HPLC;

FIG. 3 is an illustration showing the primary structure of hydrophobic surfactant protein SP-B (human sequence), illustrated with the standard, accepted one-letter code for the amino acids. The hydrophobic residues are shown in black, and the charged residues are identified [5] (SEQ ID NO: 2);

FIG. 4 is a schematic presentation of a proposed SP-B folded structure and its conjectured interaction with a phospholipid bilayer. SP-B is suggested to be a dimer of two identical 79-residue four-helix protein chains, where the hydrophobic segment of each amphipathic helix faces the lipid acyl chains. Cys48 is the third helix cross-links two monomers [67];

FIG. 5 is an illustration showing the primary structure of hydrophobic surfactant protein SP-C (human sequence). The identity of each amino acid is given by one letter code. The hydrophobic residues are shown in black, and the charged residues are identified. The two cysteine residues are palmitoylated [5] (SEQ ID NO: 3);

FIG. 6 is a schematic presentation of SP-C secondary structure and its proposed interaction with a phospholipid bilayer. The deduced NMR SP-C structure is artificially superimposed on a lipid bilayer. In the transmembrane orientation, the hydrophobic part (positions 13 through 28) interacts with the lipid acyl chains, where the basic residues at position 11 and 12 (indicated by positive charge) interact with the polar lipid head-group. The two cysteine residues at positions 5 and 6 are palmitoylated; the role of palmitoyl chains is still disputed in the literature [67];

FIG. 7a shows sequences of peptoid-peptide chimera having 14 aromatic, peptoid residues for use as SP-C Mimics, including:

```
SPCM1:
H-NhdNhd(SEQ ID NO: 1)(NpmNspeNspe)₄Nspe₂-NH₂;

SPCM2:
H-NocNoc(SEQ ID NO: 1)(NpmNspeNspe)₄Nspe₂-NH₂;
and

SPCM3:
H-(SEQ ID NO: 4)(NpmNspeNspe)₄Nspe₂-NH₂;
```

FIG. 7b shows sequences of peptoid-peptide chimera containing 14 aliphatic, peptoid residues for use as SP-C Mimics, including:

```
SPCM4:
H-NhdNhd(SEQ ID NO: 1)(Nssb)₁₄-NH₂;

SPCM5:
H-NocNoc(SEQ ID NO: 1)(Nssb)₁₄-NH₂;
and

SPCM6:
H-(SEQ ID NO: 4)(Nssb)₁₄-NH₂;
```

FIG. 7c shows sequences of completely peptoid-based SP-C Mimics;

FIG. 8 is a CD spectra of peptoid-peptide chimera of SP-C mimics SPCM2 and SPCM3 of FIG. 7a. Spectra were obtained from a Jasco 710 spectrophotometer. Samples were prepared in 2-propanol: 1% acetic acid (4:1) at a concentration of 60 µM;

FIG. 9 is a graph showing surface pressure (Π) as a function of surface area (A) of SP-C peptoid-peptide chimerae of SPCM1 and SPCM3 of FIG. 7a. Π-A isotherms were determined on a Langmuir-Wilhelmy Surface Balance at a barrier speed of 0.1 mm/sec. The samples were prepared in chloroform:water (1:1) and spread on a subphase of pure water at room temperature;

FIG. 10 shows pressure-area isotherms: in particular, FIG. 10A shows pressure-area isotherms obtained on a Langmuir-Wilhelmy Surface Balance on a water subphase at 20° C. of DPPC:POPG (7:3), 0.5 mg/ml, with 10 wt % SP-C Peptide, SP-C Mimic 2, or SP-C Mimic 3. Results indicate that the addition of SP-C mimics improves the surface activity of the lipid mixture by increasing the liftoff point and by introducing a new plateau; and FIG. 10B shows pressure-area isotherms obtained on a Langmuir-Wilhelmy Surface Balance on a water subphase at 20° C. of DPPC:POPG (7:3), 0.5 mg/ml, with 10 wt % SP-C Mimic 2 or 10 wt % SP-C Mimic 2 and 3 wt % SP-B Peptide 1. Results indicate that the addition of SP-B peptide to the lipid/SPCM2 mixture improves the biophysical activity by further increasing the liftoff point and by extending the plateau region;

Figure 15:
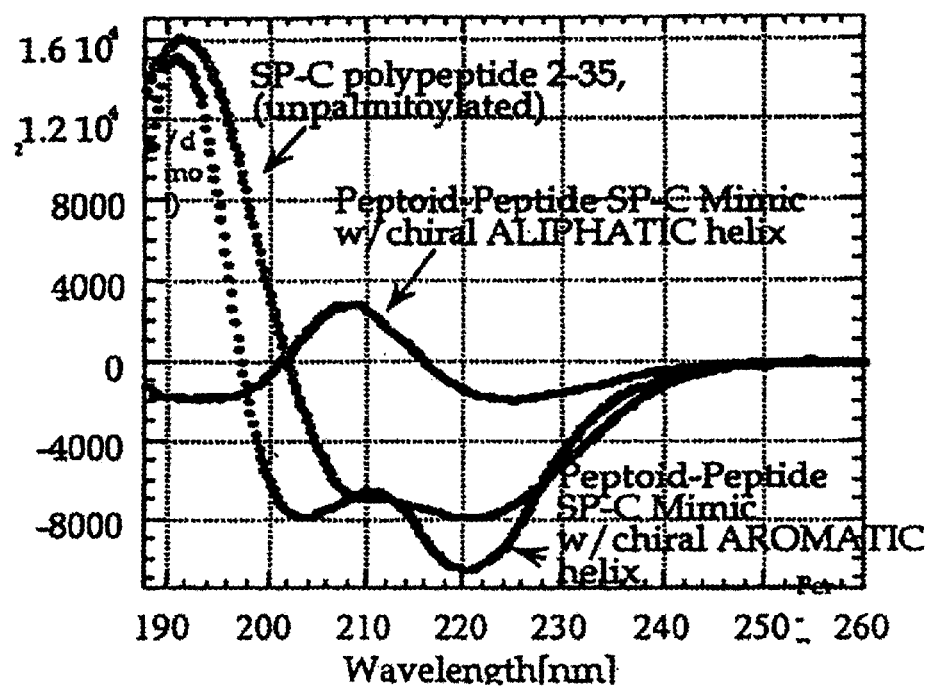
Figure 16:
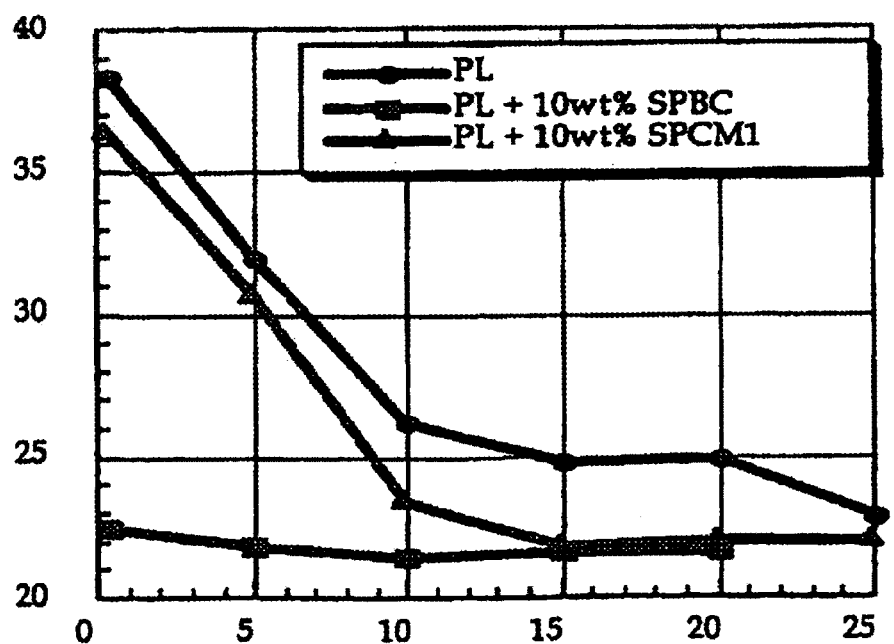
Figure 17:
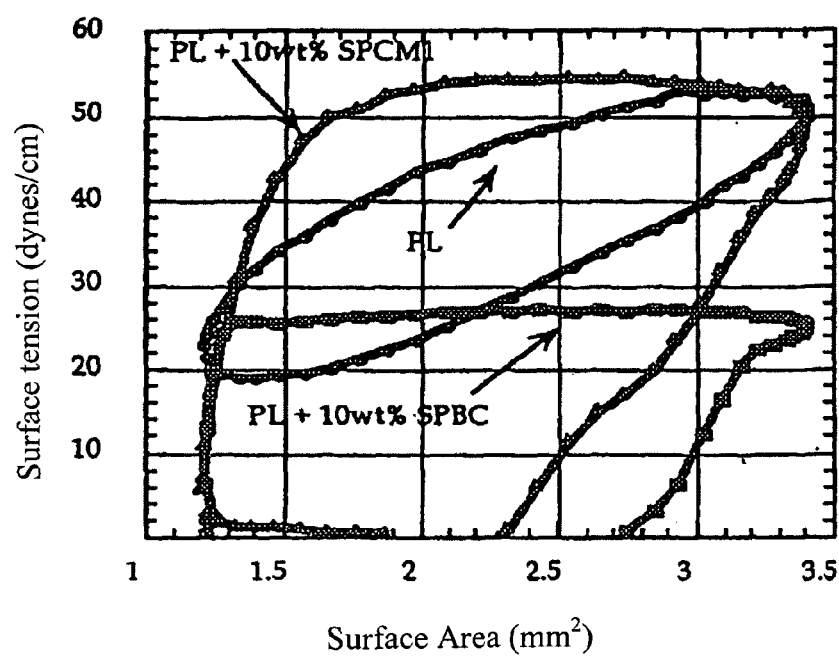

FIGS. 14A-H show fluorescence micrographs (FM) of the referenced admixtures under the conditions shown, and as further described in several of the following examples;

FIG. 15 shows CD spectra of SP-C mimics. Samples are prepared in 2-propanol: 1% acetic acid;

FIG. 16 shows adsorption surface tension as a function of time of phospholipids extracted from calf lung alone and with either 10 wt % SPBC or 10 wt % SPCM1. PL mixtures were suspended in 4 mM CaCl2, 0.15 M NaCl, and static measurements were made at 37° C. and at a bulk concentration of 1 mg/ml; and FIG. 17 shows surface tension as a function of surface area of phospholipids extracted from calf lung alone and with either 10 wt % SPBC or 10 wt % SPCM1. PL mixtures were suspended in 5 mM CaCl2, 0.15 M NaCl, and measurements were made at 37° C. during dynamic oscillations by PBS at a frequency of 20 cycles/min and at a bulk concentration of 1 mg/ml.

DETAILED DESCRIPTION OF INVENTION

Figure 1:
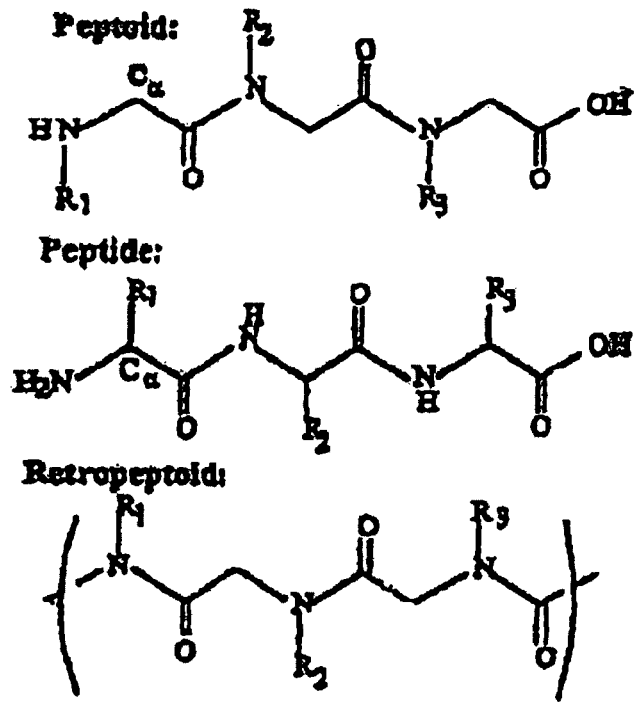

"Polypeptoids" are a class of non-natural, sequence-specific polymers representing an alternative derivative of a peptide backbone. Structurally, they differ from polypeptides in that their sidechains are pendant groups of the amide nitrogen rather than the α-carbon (see FIG. 1) [47, 48]. "Retropeptoids" are believed to have a higher probability of bioactivity when protein binding is required, as the relative positioning of sidechains and carbonyls "line up" more closely with peptides (see FIG. 1) [49]. N-Substitution prevents proteolysis of the peptoid backbone [50], giving enhanced biostability. Since polypeptoids are not proteolyzed, they are not strongly immunogenic [51].

Structural differences between peptoids and peptides do have major implications for biological mimicry. As the peptoid's backbone α-carbons do not carry substituents, the mainchain lacks chiral centers. Hence, peptoids with achiral sidechains have an equal probability of adopting right- and left-handed secondary structure. Again as a consequence of the N-substitution, peptoids lack amide protons (except for glycine analog of peptoid); thus no hydrogen-bonding network along the backbone is possible. Although poly-(N-substituted glycines) cannot form backbone-backbone hydrogen bonds, present inventors have discovered that some peptoid sequences with α-chiral sidechains do exhibit circular dichroism (CD) spectra virtually identical to those observed for polypeptide α-helices [52].

Like polypeptides, sequence-specific peptoids up to at least 50 residues in length are synthesized in high yield using a solid-phase protocol on an automated peptide synthesizer. Two approaches to peptoid synthesis can be used: a "monomer" and a "sub-monomer" method. Both can be implemented on an automated peptide synthesizer, but the latter approach is preferred as it is simpler and less expensive. In the first approach, sequence-specific polypeptoids are made by resin-bound coupling of activated α-Fmoc-protected, N-substituted glycine monomers. However, this "monomer"-based synthetic route to the peptoids is less convenient because of the requirement for chemical synthesis of α-Fmoc-protected peptoid monomers. The second route to peptoids is a simpler solid-phase protocol, called the "sub-monomer" method [48]. A major advantage of the sub-monomer method is that a great deal of front-end synthetic effort and expense is avoided because one does not need α-protected monomers.

Figure 2:
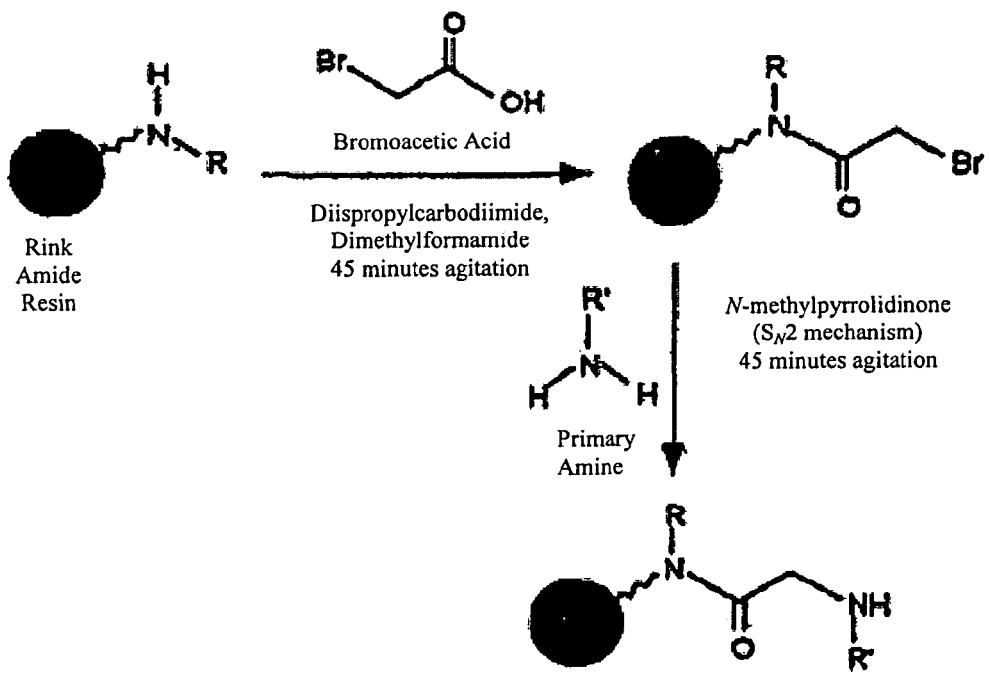

The sub-monomer synthetic protocol, developed by Zuckermann [48], is shown in FIG. 2. Each monomer is assembled from two readily-available sub-monomers. Rink amide resin is acetylated by carbodiimide-activated α-bromoacetic acid. The acetylated resin undergoes $S_N2$ displacement by a primary amine to introduce the desired sidechain [53]. Hundreds of amine sub-monomers are available commercially, so peptoid synthesis by the sub-monomer route provides access to great diversity in functionalized poly(N-substituted glycines), with modest cost and effort. However there are cases, where the desired primary amines need to be synthesized and whose reactive functionalities need to be protected. Average sub-monomer coupling efficiencies are greater than 98.5% if sidechains are not overly bulky, and often as high as 99.6%, comparable to coupling efficiencies attained in Fmoc peptide synthesis.

It is a simple matter to alternate between "monomer" and "sub-monomer" peptoid synthesis protocols within a single automated peptide synthesizer run. This is an important capability for two reasons. First, there exist primary amine precursors to the proteinogenic sidechains that are chemically unstable and/or difficult to incorporate by sub-monomer methods without side reactions. For these residues, α-Fmoc-protected N-substituted analogs of these sidechains are prepared and incorporated into peptoids by standard Fmoc monomer methods. Second, ability to alternate between monomer and sub-monomer protocols allows the synthesis of a peptoid-peptide chimera, allowing simultaneous optimization of bioactivity and in vivo stability. In other words, this allows one to create stretches of peptide residues and peptoid residues in the same molecule.

SP-B is a small, hydrophobic protein comprised of 79 amino acids with a high content of cysteine [54]. Its primary structure has been highly conserved in mammals [5]. In native SP-B, seven cysteine residues form a unique disulfide pattern of three intramolecular bonds and one intermolecular disulfide bond, resulting in the formation of SP-B dimers [55, 56].

Figures 3, 4:
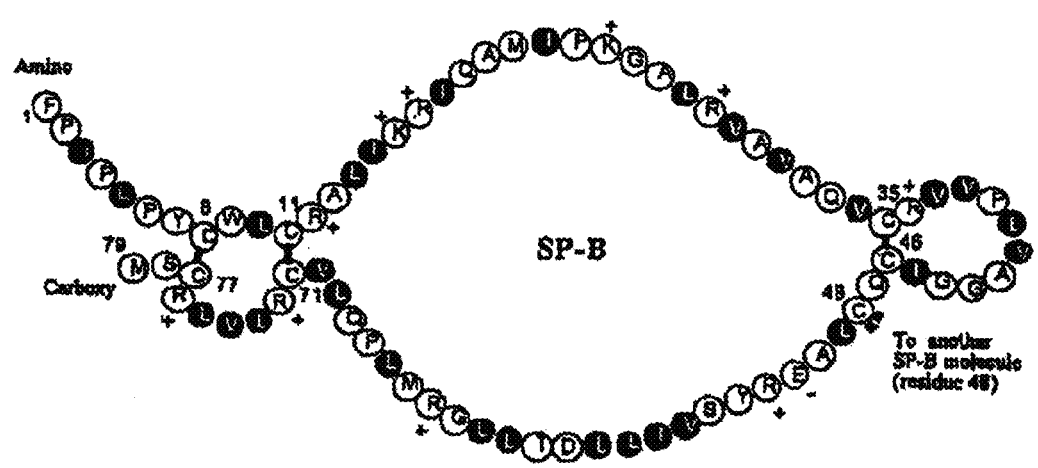

Several positively-charged sidechains in SP-B are essential for activity [57]; interactions of these groups with negatively-charged PG molecules speed up phospholipid adsorption to air-water interfaces. CD spectra suggest that SP-B secondary structure is dominated by α-helices; but the three-dimensional structure of the molecule has not been determined [41, 58]. The four helices are predicted to be amphipathic, where one helical face is hydrophobic, and the other relatively hydrophilic. The schematic picture shown in FIG. 4 represents a hypothesized secondary and tertiary structure of an SP-B monomer, showing a proposed helix-turn-helix motif. A proposed SP-B interaction with phospholipid bilayers is also shown. It has been hypothesized that SP-B proteins reduce surface tension on alveoli by increasing lateral stability of the phospholipids [57].

Figure 5:
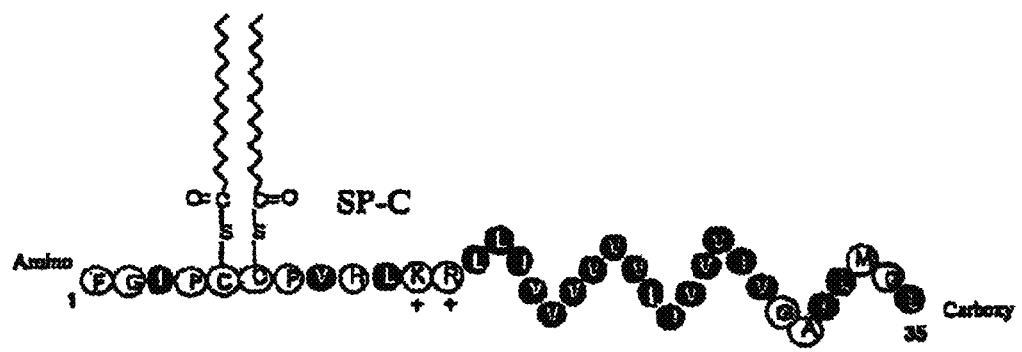
Figure 6:
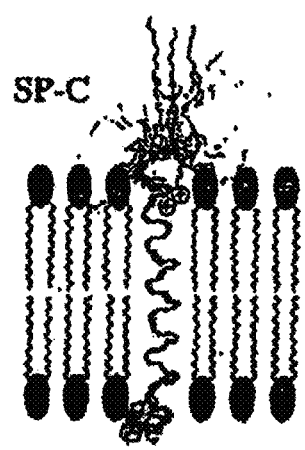
Figure 8:
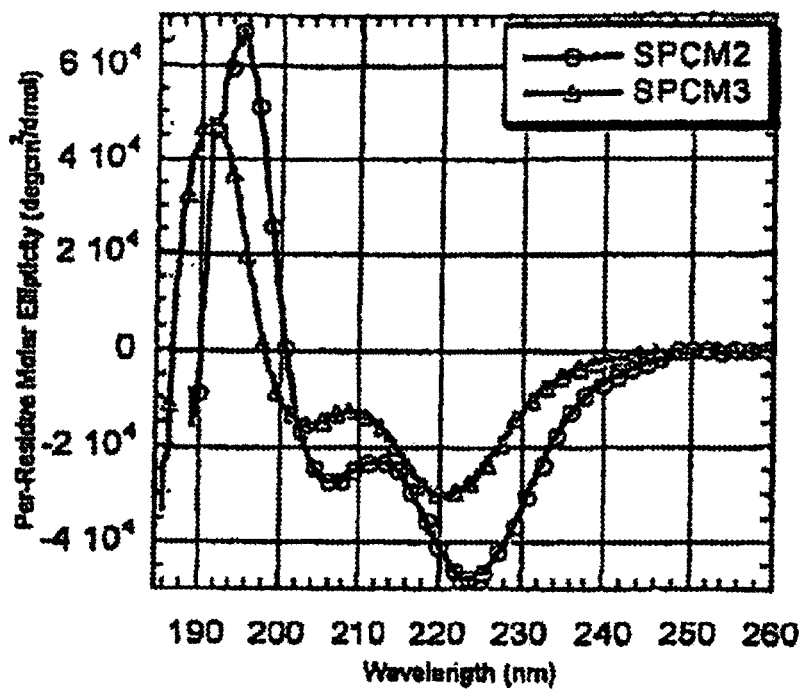

The other hydrophobic surfactant-associated protein is SP-C whose primary sequence is shown in FIG. 5. If removed from its association with lipids, this hydrophobic 35mer peptide is soluble in organic solvents only [59]. Two-thirds of the protein consists of a long, continuous valyl-rich hydrophobic stretch that adopts an α-helical structure, as evidenced by CD and NMR [60-62] and is of a length that spans the DPPC bilayer as depicted in FIG. 6. Consistent with this, it has been shown that the SP-C α-helix is oriented parallel to lipid acyl chains [64]. Palmitoylation of SP-C's two cysteines at positions 5 and 6 in the sequence may promote interactions with lipid acyl chains in neighboring, stacked lipid bilayers [65]; however the physiological function of the palymitoyl chains and their necessity for in vivo efficacy has yet to be fully determined [45, 46]. The two adjacent, positively-charged lysine and arginine residues at positions 11 and 12 most likely interact with the phospholipid headgroups [66].

The present invention provides peptoid mimics of the surfactant proteins SP-B and SP-C that endow a synthetic, biomimetic exogenous lung surfactant replacement with clinical efficacy nearly equaling that of currently-used animal-derived formulations.

The helical, amphipathic nature of the SP proteins is known to be important for obtaining appropriate biophysical properties. In the case of SP-B, studies also indicate an importance of distribution of hydrophobic and charged residues around the helical circumference, for obtaining optimal surface activity for the shortened biomimetic sequence SP-B (1-25). In one aspect of the present invention, to mimic SP-B amino-terminal residues 1-25, circumferentially amphipathic polypeptoids with achiral and chiral hydrophobic faces of the helices are provided, taking into account differences in helical pitch between peptoids and peptides. In the case of SP-C, investigators have shown the importance of hydrophobic, helical regions.

In another aspect of the present invention, to mimic SP-C, longitudinally amphipathic peptoid mimics with chiral and achiral hydrophobic "tails" are provided. Such peptoids with hydrophobic, helical regions are of a length to almost exactly span a lipid bilayer as the natural helical SP-C peptide is proposed to do. The significance of SP-C palmitoyl chains are currently under debate, thus SP-C peptoid mimics with different chain lengths at this position are provided. The present invention also provides an array of peptide analogs with families of sidechains varied at certain positions within the class of aliphatic residues, aromatic residues, charged residues, etc. In particular and without limitation, the present invention provides simple and inexpensive mimics of SP-B (1-25) and SP-C (5-32) with excellent biomimetic performance.

Yet another embodiment of the present invention provides SP-mimics (i.e., peptide analogs containing at least one peptoid residue) containing both peptide and peptoid segments (i.e., chimera). In one particular embodiment, the hydrophobic regions of the molecule are, preferably, peptoid-based, while the remaining regions are peptide-based. The presence of the peptoid segment increases the chimera's efficacy and protease-resistance, and hence increase its bioavailability as compared to a solely peptide-based mimic.

Another embodiment of the present invention provides a peptide analog composition comprising a mixture of peptide-based and peptoid-based SP-mimics in LS replacements. The rationale for this idea is based on the fact that peptide SP-mimics have been demonstrated to promote rapid adsorption acid respreading of LS to the air-water interface, thereby providing the rapid response needed to enable breathing. However, because peptides are subjected to biodegradation by proteases, their effectiveness as spreading agents is reduced within a short time. Peptoids, on the other hand, have been shown to be protease-resistant, and hence offer the advantage of long-term bioavailability. Therefore, the mixture of peptide-based and peptoid-based SP-mimics is an alternative biomimetic spreading agent for LS treatment.

Yet another embodiment of the present invention provides a pulmonary surfactant composition comprising any of the aforementioned SP-mimics and a lipid admixture. Typically each of the aforementioned SP-mimics are added in varying concentration (ranging from 1 wt % to 20 wt %) to an optimal lipid admixture. The lipid admixture is composed of various synthetic lipids and minor agents in different composition. Lipids may include dipalmitoylphosphatidylcholine, phosphatidylcholine, phosphatidylglycerol, phosphatidylethanolamine, phosphatidylinositol, phosphatidylserine, and cholesterol. Minor agents include palmitic acids.

Several unique properties of polypeptoids make them an attractive replacement for the surfactant proteins SP-B and SP-C. Their protease resistance, and hence low immunogenicity, offer advantages over animal or sequence-altered peptides, which could potentially elicit an immune response that would result in the production of cross-reactive antibodies [18], or rapid inactivation via complexation with antibodies. Furthermore, the protease resistance increases the bioavailability and efficacy of peptoid-based SP-mimics as compared to peptide mimics. Moreover, the use of synthetic peptide analogs eliminates risks that are currently associated with surfactant replacement using animal-derived formulations, including disease transmission risk from surfactant contaminated with pathogens, surfactant inhibition by immunological complexes, and improved efficacy as compared to synthetic formulations.

Three sets of specific SP-C mimics (i.e., protein analog spreading agents comprising at least one peptoid residue) are illustrated in FIGS. 7*a, b, c*. The first two sets are peptoid-peptide chimerae that have chiral, hydrophobic peptoid stretches. The first set has a peptoid region of fourteen chiral aromatic residues with helical secondary structure (FIG. 7*a*). This chimera set contains the peptide (SEQ ID NO: 4) (#5-12 of SP-C), and variants with the substitution of octylamine (Noc) or hexadecylamine (Nhd) for the palmitoylated cysteine residues naturally found at positions 5 and 6. In the second set of mimics, the peptoid region is comprised of chiral aliphatic side chains in place of chiral aromatic groups, with the same attached peptide (FIG. 7*b*). The third design is a completely peptoid-based SP-C mimic with the sequence illustrated in FIG. 7*c*.

Additional objects, advantages, and novel features of this invention will become apparent to those skilled in the art upon examination of the following examples thereof, which are not intended to be limiting.

EXAMPLES OF THE INVENTION

The following non-limiting examples and data illustrate various aspects and features relating to the polypeptoid spreading agents/surfactant compositions and/or methods of the present invention, including the preparation and administration of such materials, as are available through the synthetic methods/techniques described herein. In comparison with the prior art, the present methods and spreading agents/compositions provide results and data which are surprising, unexpected and contrary to the art. While the utility of this invention is illustrated through the use of several spreading agents/compositions and residues which can be incorporated therein, it will be understood by those skilled in the art that comparable results are obtainable with various other agents/compositions and residues, as are commensurate with the scope of this invention.

Example 1

The peptoid-peptide chimerae and peptoid SP-mimics were synthesized on a PE-Biosystems model 433A® automated peptide synthesizer using the sub-monomer and monomer protocol, with the sidechains shown in the sequence mentioned above. Synthesis was on 0.25 mmol Rink amide resin (substitution, ca 0.5 mmol/g, NovaBiochem, San Diego Calif.). After removal of the first Fmoc protecting group from the resin, the following 90-minute monomer addition cycle is performed: the amino-resin is bromoacetylated by adding 4.1 mL of 1.2M bromoacetic acid in DMF plus 1 mL of N,N'-diisopropylcarbodiimide. The mixture is vortexed in the synthesizer's reaction vessel for 45 minutes, drained, and washed with DMF (4×7 mL). 6 mL of 1M primary amine in NMP is added to introduce the desired sidechain and agitated for 45 min. Depending on the difficulty of incorporation of the primary amine, the coupling time may be extended to 2 hours. In the case when an Fmoc-protected monomer is introduced, an alternative protocol was used that involved the reaction of 10 equivalents of monomer, 10 equivalents of HATU, and 20 equivalents of DIEA in 6 mL of DMF for a reaction time of 2 hours. After the addition of the monomer, the Fmoc-protecting group is removed with 20% piperidine in DMF (6 mL) for 20 minutes. These two cycle types are repeated until the desired sequence is attained. After the last addition, the peptoid or chimera is washed with $CH_2Cl_2$ and then cleaved with the appropriate cleavage mixture as determined by the types of protecting groups present. Typically this mixture includes trifluoracetic acid (TFA), water, and scavengers such as thioanisole, 1,2-ethandithiol, and crystal phenol. The reaction time varies from 30 minutes (no protecting groups) to 2 hours (protecting groups). After the molecule is cleaved, it is diluted into water, frozen, and lyophilized.

Example 2

The crude peptoid of Example 1 was dissolved in acetonitrile/water and analyzed by gradient reversed-phase HPLC on C4 packing (Vydac, 5 μm, 300 Å, 4.6×250 mm). A linear gradient of 0-100% B in A was run over 60 min at a flow rate of 1 mL/min (solvent A=0.1% TFA in water, B=0.1% TFA in isopropanol) at 60° C. Preparative HPLC was performed on a Vydac C4 column (15 μm, 300 Å, 10×250 mm) using the same solvent system; peaks were eluted with a linear gradient of 0-100% B in A over 45 min at 8 mL/min. Depending on the hydrophobicity of the molecule alternative gradients are used with different mobile phases including acetonitrile and water. The samples were purified to >99%. ES or MALDI-TOF mass spectroscopy was used to confirm chemical identity. Circular dichroism spectroscopy (CD) was carried out on a JASCO J-720 instrument. 60 μM samples were analyzed in a cylindrical quartz cuvette with a path length of 0.02 cm (Hellma, Forest Hills, N.Y.). Surface activity measurements were performed on Langmuir-Wilhelmy Surface Balance and a Pulsating Bubble Surfactometer. The circular dichroism (CD) spectra of the peptoid-peptide chimera are shown in FIG. 8. The samples were prepared in 2-propanol: 1% acetic acid (4:1). SPCM2 and SPCM3 exhibit the characteristic signatures of an α-helical structure with trans-amide bonds (just slightly blue-shifted, more intense, and more well-defined than the peptide CD).

Example 3

Figure 9:
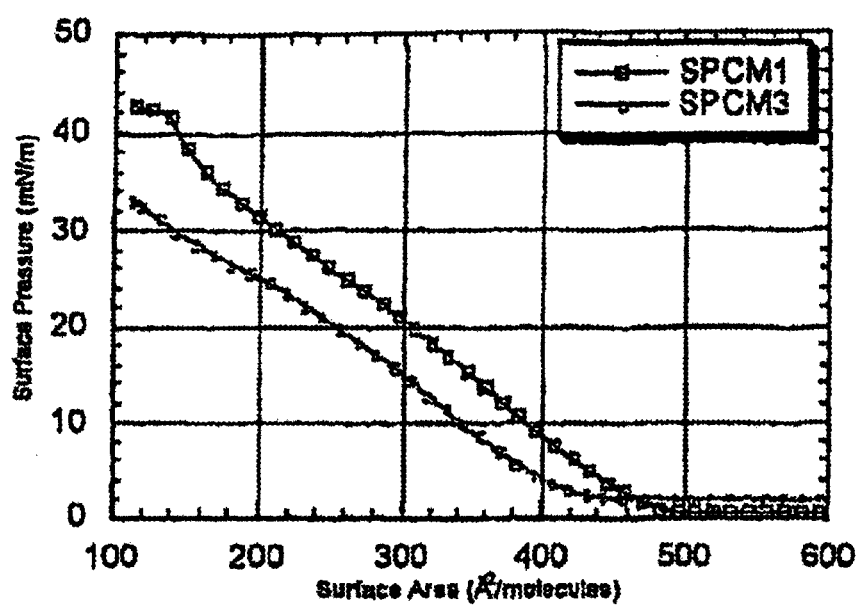

The surface pressure-area isotherms of SP-C mimics as measured on a Langmuir-Wilhelmy Surface Balance ("LWSB") are shown in FIG. 9. The samples were prepared in chloroform:methanol (1:1) and spread on the trough filled with water (subphase). The peptoid-peptide chimera SPCM1 and SPCM3 have comparable (but not identical) surface activities (high collapse pressure) in comparison to the SP-C peptide as found in literature. The activity of the aforementioned SP-C mimics in combination with phospholipids is shown in FIGS. 10A-B. The admixture is composed of DPPC:DPPG (7:3) with 0.4 mole % of SP-C mimics. The results show that the addition of the mimic improves the surface activity as indicated by the decrease in hysteresis between the first and second compression-expansion cycles. This is significant because it suggests that less material is being lost into the subphase, which has been an issue associated with films composed of lipids alone.

Example 4

Figure 11:
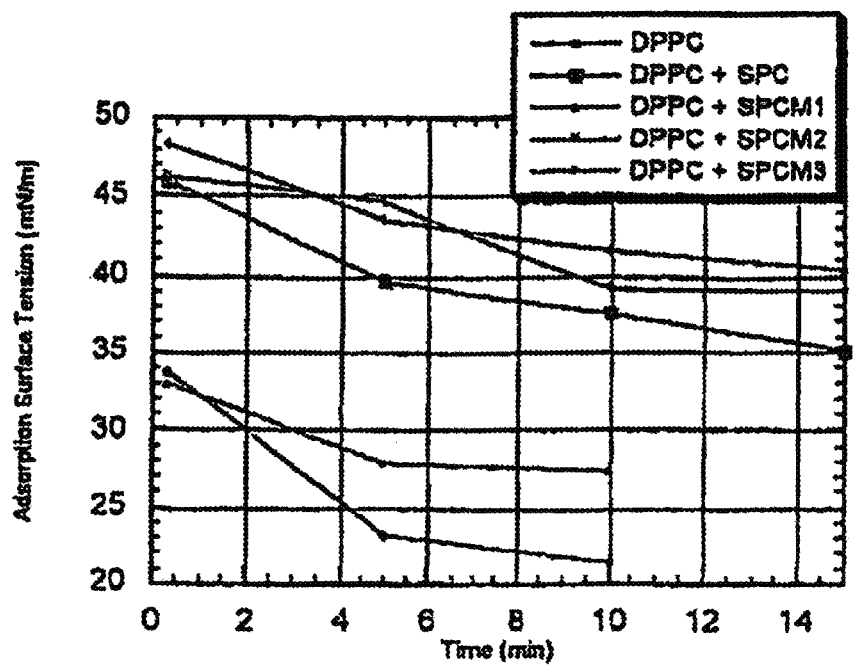
FIG. 11 is a graph showing adsorption surface tension as a function of time of DPPC with 3 wt % peptoid-peptide chimera of FIG. 7a, in 5 mM $CaCl_2$, 0.15 M NaCl was measured at 37° C. by a pulsating bubble surfactometer at a frequency of 20 cycles/min and a bulk concentration of 1 mg/ml.

Equilibrium and dynamic surface tension measurements of mimics and lipids were made using a pulsating bubble surfactometer (Electronetics, Amherst, N.Y.) with an external water bath. Equilibrium surface tension measurements were performed under static conditions, before carrying out dynamic measurements. Samples were prepared in aqueous buffer; e.g., 15 M NaCl and 50 mM $CaCl_2$. Samples were loaded using a disposable syringe and a bubble of 0.40 mm radius was formed using a needle valve. Bubble pressure was recorded as a function of time for a minimum of 10 min., until the surface tension reached equilibrium. Results of these measurements are depicted in FIG. 11. Note: A "good" exogenous lung surfactant replacement quickly reduces the surface tension to a low value (~25 dynes/cm), whereas natural lung surfactant reduces the surface tension even further, to ~20 dynes/cm. A rapid approach to a low equilibrium surface tension is best. SPCM1 reduced equilibrium surface tension to a lower value than natural SP-C peptide, suggesting that it adsorbs more rapidly to the interface than the natural surfactant peptide. It is believed that this is because the natural SP-C peptide tends to become aggregated into B-sheets, both during and after its isolation from animal lungs.

Example 5

Figure 12:
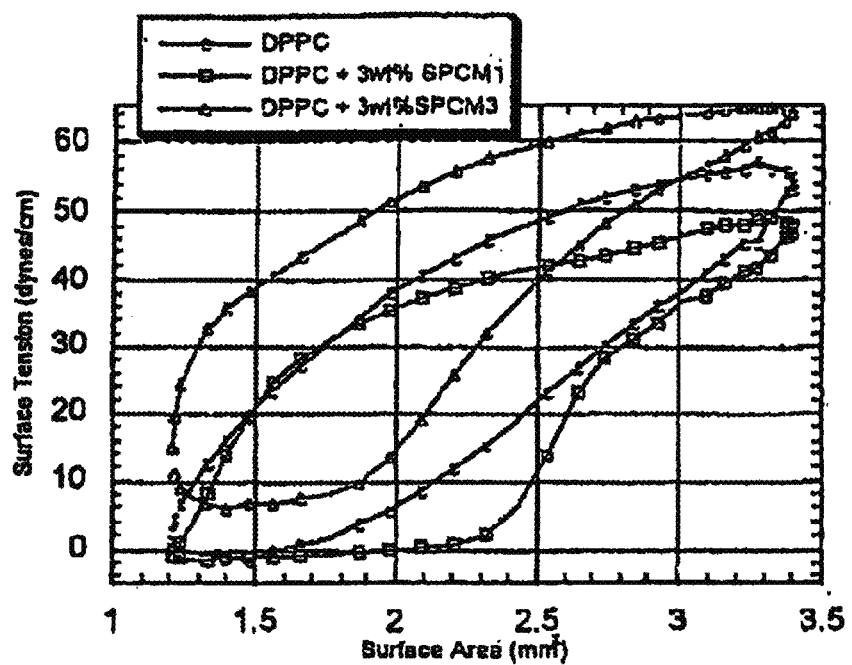
FIG. 12 is a graph showing surface tension as a function of interfacial surface area for DPPC alone, as well as DPPC+ SPCM1 (3% by weight) or SPCM3 (3% by weight), in 5 mM $CaCl_2$, 0.15 M NaCl was measured at 37° C. during dynamic oscillations by a pulsating bubble surfactometer at a frequency of 20 cycles/min and a bulk concentration of 1 mg/ml.

Dynamic measurements of surface tension as a function of surface area were made at 37° C. and bulk concentrations of 1 mg/ml. Bubble radius was cycled between 0.31 mm and 0.52 mm at an oscillation frequency of 20 cycles per minute. Results of DPPC alone and DPPC plus peptoid-based SP-C mimics (SPCM1 or SPCM3) are shown in FIG. 12, DPPC monolayers are known to reach very low surface tension (essentially, a surface tension of "zero") upon compression. However, pure DPPC does not function well as an exogenous lung surfactant replacement because DPPC monolayers are very rigid; hence, they exhibit a "tight" loop of surface tension vs. interfacial surface area, and require substantial surface area compression (>70%) before surface tension reaches "zero." Furthermore, DPPC re-spreads poorly upon subsequent cycling. In the lungs, compression of alveolar surface area is by at most 50%, so it is important that "zero" surface tension is reached upon 50% compression or less. In vivo, the natural lung surfactant proteins SP-B and SP-C ensure that this is the case. Peptoid-based SP-C mimics of the present invention improve the re-spreading of DPPC alone and show a dynamic profile similar to native SP-C. An advantage of a peptoid-based system is the added potential of enhanced bioavailability.

Example 6

Figure 13:
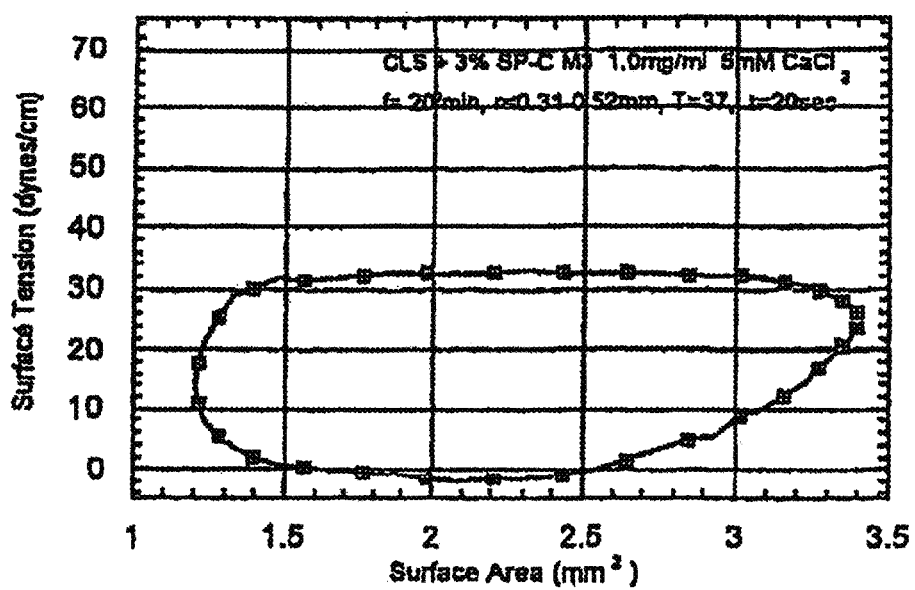
FIG. 13 is a graph showing surface tension as a function of interfacial surface area for cell lung surfactang (CLS)+ SPCM3 (3% by weight) in 5 mM $CaCl_2$, 0.15 M NaCl was measured at 37° C. during dynamic oscillations by a pulsating bubble surfactometer at a frequency of 20 cycles/min and a bulk concentration of 1 mg/ml.
Figure 14:
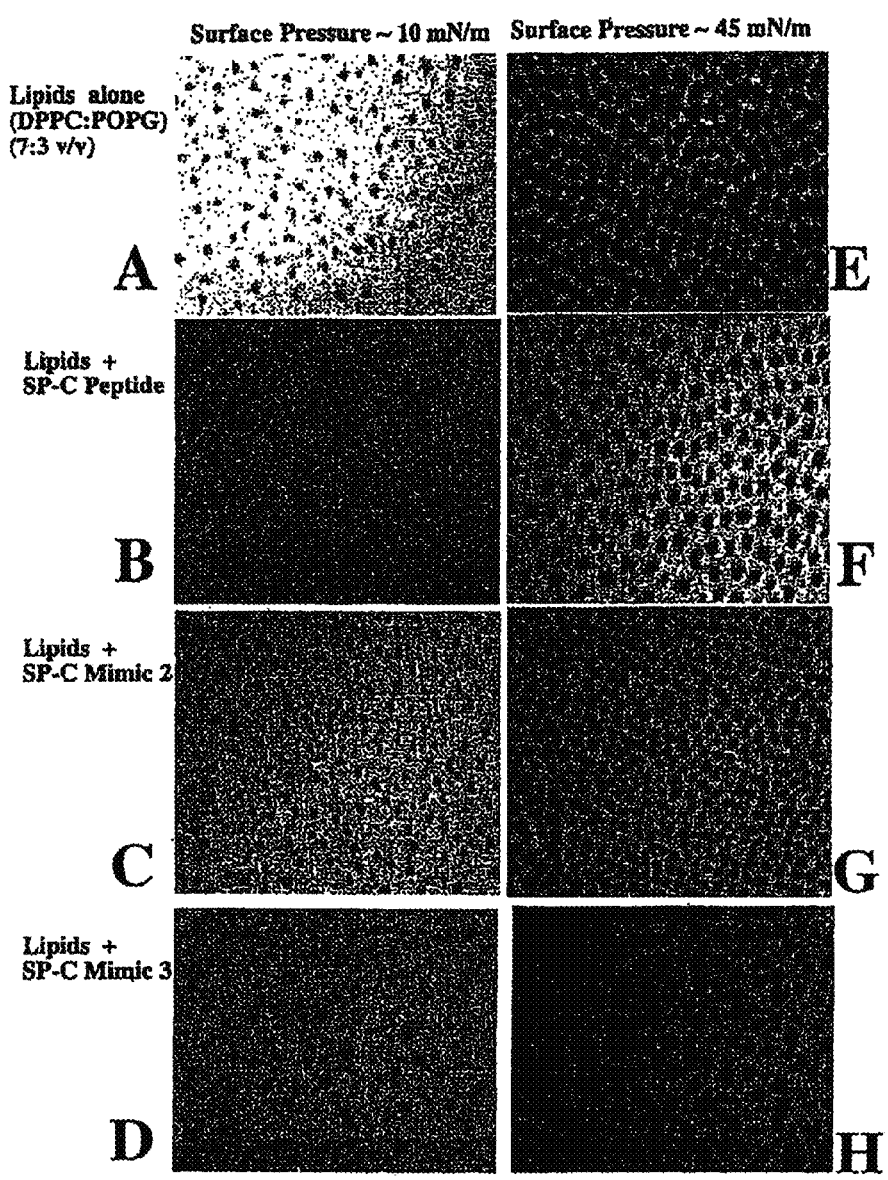

Since natural surfactant production will occur within 96 hours, it is important to demonstrate that peptoid mimics will not adversely affect natural surfactant. FIG. 13 demonstrates that the addition of SP-C mimics to whole calf lung surfactant (CLS) does not appear to adversely effect the static and dynamic behavior of CLS. FIG. 13 shows the dynamic interfacial properties of CLS+SPCM3 (3% by weight). Similar to CLS alone (data not shown), this mixture reaches a minimum surface tension of less than 1 dyne/cm after a small compression. The maximum surface tension at an oscillation frequency of 20 cycles/min is around 30 dynes/cm.

Example 7

This example shows a successfully synthesized, purified and characterized completely peptoid-based SP-C mimic (referred to as SPCM3, sequence given below) with a diversity of biomimetic, proteinogenic sidechains. SPCM3 is designed to serve as an analog of the human SP-C protein (residues 5-32). Peptoid oligomers with chiral, aromatic Nspe residues are known from 2D-NMR structural studies to adopt a polyproline type I-like structure that has cis-amide bonds, a helical pitch of ~6 Å, and a repeat of 3 residues per turn (P. Armand, et al., PNAS 1998; K. Kirshenbaum et al., PNAS 1998). Hence, the design of this peptoid-based SP-C mimics took into account differences in helical pitch of peptide α-helices (5.4 Å) and peptoid helices (6 Å for aromatic-based and 6.7 Å for aliphatic-based (the latter result was determined recently by crystallography).) The dependence of peptoid helical structure and stability on the number of Nspe residues in the chain was recently accepted for publication in JACS. Based on knowledge of peptoid helical parameters, the number of monomers in the hydrophobic helical stretch of the molecule (14 Nspe residues) was selected to create a helix ~37 Å in length, mimicking the trans-bilayer helix that is found in the natural SP-C peptide.

SPC Mimic 3 Chiral Aromatic Helical Stretch and Achiral Hydrophilic Stretch

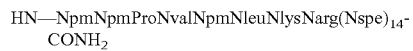

Two phenylmethyl (Npm) residues were substituted in SPM3 for the natural SP-C palmityl groups. After purification of the full-length peptoid 22mer by preparative HPLC, the purity and correct molar mass (3308 Da) were confirmed by analytical HPLC and electrospray mass spectroscopy, respectively.

Example 8

This example provides in vitro biophysical characterization of SPCM3, SPCM2 (peptide-peptoid chimera, sequence below), and synthetic SP-C peptide (control). All three molecules show CD spectra that are characteristic of helical secondary structure, as shown in FIG. 15. FIG. 10A displays surface-pressure area Π-A) isotherms of a lipid admixture (DPPC:POPG, 7:3, 0.5 mg/ml) with or without the addition of SP-C mimics (10 wt %), obtained on a Langmuir-Wilhelmy surface balance (LWSB). The addition of either SP-C peptide or the peptoid-based SP-C mimics is clearly seen to improve the surface activity of the synthetic lipid admixture, as indicated by the increased liftoff point (evidence of rapid adsorption of the materials to the air-water interface). More telling, upon addition of both the synthetic peptide and the peptoid mimics, observe the introduction of a plateau region in the isotherm, which is an indication of the presence of a new phase transition. The occurrence of this transition is a unique signature of the interaction of surfactant proteins with phospholipids, and the data of this example shows that surface-active peptoids also introduce this plateau. The Π-A isotherms obtained with peptoid-based SP-C mimics are highly similar to those obtained with the SP-C peptide, suggesting that the mimics are able to capture some critical surface-active features of SP-C.

SPC Mimic 2 N-(SEQ ID NO: 4)(Nssb)$_{15}$-C

Example 9

LWSB experiments show the effects of the addition of the 25mer SP-B peptide 1 (SPB1) along with peptoid-based SP-C mimic 2 (SPCM2). In FIG. 10B, we observe that the addition of 3 wt % SPB1 to the lipid admixture containing 10 wt % SPCM2 dramatically improves the surface activity as indicated by further increasing the liftoff point and the extension of the plateau. From this result, we can conclude that a promising lung surfactant formulation can contain both SP-B and SP-C mimics.

Example 10

To further investigate the similarity in biophysical performance of the lipid admixtures containing different types of SP-C mimics, as indicated by the Π-A isotherms, this example shows use of fluorescence microscopy (FM) in conjunction with the LWSB to study phase morphology of these lipid/peptide and lipid/peptoid cocktails. A small fraction of the DPPC lipid (1 mol %) is tagged with a fluorescent dye that preferentially partitions to less ordered regions. Hence, FM images typically will show contrast between dark and light regions, with the dark regions corresponding to the liquid condensed phase (LC) and light regions corresponding to the liquid expanded phase (LE). FIGS. 14A-H display FM images at surface pressures of around 10 mN/m (left) and 45 mN/m (right) for lipids alone (panels A and D), lipids with 10 wt % SP-C peptide (panels B and E), lipids with 10 wt % SPCM2 (panels C and F), and lipids with 10 wt % SPCM3 (panels D and G). These FM images show that the addition of SP-C mimics results in dramatically different phase morphology of the surface film in comparison to that observed for phospholipids alone, and which is similar to that of the natural SP-C peptide: direct evidence that both of the peptoid-based SP-C mimics tested have substantial biomimetic interaction with DPPC and POPG lipids.

Example 11

With phospholipids alone (panels A and E), there is observed a typical phase behavior of the film in which dark LC phases that appear as scattered spots in panel A increase in size and density upon surface compression, so that the extent of the more fluid (light) LE region is reduced (panel E). A dark film such as that shown in panel E is enriched in DPPC (POPG is "squeezed out"), highly ordered, and will not respread well upon subsequent surface expansion. In comparison, inspection of the images taken with added SP-C peptide show that the interaction of the protein with lipids acts to retain the fluidity of the film upon compression, as evidenced by the larger extent of light LE regions and the decrease in LC domain size in Panel F, the critical behavior that must be mimicked for effective biophysical functioning of a surfactant replacement. ([1]A. Kramer et al., 'Distribution of the surfactant-associated protein C within a lung surfactant model investigated by near-field optical microscopy' Biophysical Journal, Vol. 78, 2000, 458-465. A. von Nahmen et al., 'The phase behavior of lipid monolayers containing pulmonary surfactant protein C studied by fluorescence microscopy' European Biophysical Journal, Vol. 26, 1997, 359-369. J. Perez-Gil et al., 'Pulmonary surfactant protein SP-C causes packing rearrangements of dipalmitoylphosphatidylcholine in spread monolayers' Biophysical Journal, Vol. 63, 1992, 197-204.) Note that all of the images on the right-hand side that include SP-C or its mimics (Panels F, G, and H) reflect the phase morphology observed in the plateau region of the Π-A isotherms as shown in FIG. 10A.

Example 12

The FM images taken of the phase behavior of peptoid mimics in combination with phospholipids in a surface film show the same type of phase behavior as that observed for SP-C peptide in combination with lipids. (Refer to Panels F, G, and H, which all show a greater extent of light LE phase and a reduction in the average size of the dark LC domains, in comparison to panel E.) Most particularly, the phase behavior of SPCM3 under compression (panel H) is highly similar to that of SP-C peptide (panel F) suggesting biomimetic behavior and function of this peptoid molecule. Based on a comparison of the Π-A isotherms and the FM images, the peptoid-based SP-C mimics appear to capture critical features of the SP-C peptide. These results indicate that peptoid-based spreading agents hold great promise for use as a functional, bioavailable, lung surfactant formulation. The protease-stability of the peptoids, in addition to the stability of their helical conformations in solution (unlike SP-C peptide, which is prone to misfold and aggregate.) (See, C. W. Wu, T. J. Sanborn, R. N. Zuckermann, A. E. Barron, 'Peptoid oligomers with α-chiral aromatic sidechains: Effects of chain length on secondary structure' Journal of the American Chemical Society, accepted for publication) make them uniquely suited to biomedical application of the present structured, amphipathic oligomers for the treatment of respiratory distress in premature infants and potentially, adults.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent sequences, structures, functions, ranges or steps to those claimed, whether or not such alternate, interchangeable and/or equivalent structures, functions, ranges or steps are disclosed herein, and without intending to publicly dedicate any patentable subject matter.

We claim:

1. An SP-C mimic compound comprising an N-terminal component of 2 residues selected from N-substituted glycine residues $N_{oc}$, $N_{pm}$ and $N_{hd}$, and Phe and combinations thereof; a sequence selected from peptide sequence ProValHisLeuLysArg (SEQ ID NO: 1) and biomimetic sequences thereof wherein said biomimetic sequences are peptide sequences of SEQ ID NO: 1 wherein at least one peptide sequence residue of SEQ ID NO: 1 is replaced with an N-substituted glycine residue, said N-substituent is the α-carbon sidechain moiety of said replaced peptide sequence residue; and a hydrophobic C-terminal component of said compound of about 12 to about 20 N-substituted glycine residues selected from $N_{pm}$, $N_{spe}$ and $N_{ssb}$ residues and combinations thereof.

2. The compound of claim 1 wherein said N-terminal component comprises residues are selected from 2 $N_{oc}$ residues and 2 $N_{hd}$ residues.

3. The compound of claim 2 wherein said C-terminal compound component is 13-15 residues.

4. The compound of claim 2 wherein all said peptide sequence residues are replaced, and said biomimetic sequence is $N_{Pro}N_{Val}N_{His}N_{Leu}N_{Lys}N_{Arg}$.

5. The compound of claim 1 in a pulmonary surfactant composition.

6. The compound of claim 5 present at about 1 to about 20 weight percent of said composition.

7. An SP-C mimic compound comprising an N-terminal component of 2 residues selected from N-substituted glycine residues $N_{oc}$, $N_{pm}$ and $N_{hd}$ and combinations thereof; a biomimetic peptoid sequence $N_{pro}N_{Val}N_{His}N_{Leu}N_{Lys}N_{Arg}$; and a hydrophobic C-terminal component of said compound of about 12 to about 20 N-substituted glycine residues selected from $N_{pm}$, $N_{spe}$ and $N_{ssb}$ residues and combinations thereof.

8. The compound of claim 7 wherein said N-terminal component residues are selected from 2 $N_{oc}$ residues and 2 $N_{hd}$ residues.

9. The compound of claim 8 wherein said C-terminal compound component is 13-15 residues.

10. The compound of claim 7 in a pulmonary surfactant composition.

11. The compound of claim 10 present at about 1 to about 20 weight percent of said composition.

12. An SP-C mimic compound comprising an N-terminal component of 2 residues selected from N-substituted glycine residues $N_{oc}$, $N_{pm}$ and $N_{hd}$ and combinations thereof; a biomimetic peptoid sequence $N_{Pro}N_{Val}N_{His}N_{Leu}N_{Lys}N_{Arg}$; and a hydrophobic C-terminal component of said compound of 12 to 14 N-substituted glycine residues selected from $N_{pm}$, $N_{spe}$ and $N_{ssb}$ residues and combinations thereof.

13. The compound of claim 12 wherein said N-terminal component residues are selected from 2 $N_{oc}$ residues and 2 $N_{hd}$ residues.

14. The compound of claim 13 wherein said C-terminal compound component is 14 residues.

15. The compound of claim 12 incorporated into a pulmonary surfactant composition.

16. The compound of claim 15 present at about 1 to about 20 weight percent of said composition.

* * * * *

SEQUENCE LISTING

<160> NUMBER OF SEQ ID NOS: 4

<210> SEQ ID NO 1
<211> LENGTH: 9
<212> TYPE: PRT
<213> ORGANISM: Homo sapiens
<220> FEATURE:
<221> NAME/KEY: Misc._Feature
<222> LOCATION: (1)..(2)
<223> OTHER INFORMATION: Either Phe, Cys with an attached palmitoyl
      residue, or N-substituted peptoid
<220> FEATURE:
<221> NAME/KEY: Misc._Feature
<222> LOCATION: (9)..(9)
<223> OTHER INFORMATION: One or more N-substituted glycine residues,
      such substituents including but not limited to proteinogenic amino
      acid side chain or a carbon analog thereof

<400> SEQUENCE: 1

Xaa Xaa Pro Val His Leu Lys Arg Gly
1               5

<210> SEQ ID NO 2
<211> LENGTH: 79
<212> TYPE: PRT
<213> ORGANISM: Homo sapiens

<400> SEQUENCE: 2

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Arg Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met
65                  70                  75

<210> SEQ ID NO 3
<211> LENGTH: 35
<212> TYPE: PRT
<213> ORGANISM: Homo sapiens

<400> SEQUENCE: 3

Phe Gly Ile Pro Cys Cys Pro Val His Leu Lys Arg Leu Leu Ile Val
1               5                   10                  15

Val Val Val Val Val Leu Ile Val Val Val Ile Val Gly Ala Leu Leu
            20                  25                  30

Met Gly Leu
        35

<210> SEQ ID NO 4
<211> LENGTH: 24
<212> TYPE: PRT
<213> ORGANISM: Homo sapiens
<220> FEATURE:
<221> NAME/KEY: Misc._Feature
<222> LOCATION: (9)..(24)
<223> OTHER INFORMATION: Fifteen N-substituted glycine residues, each
      such residue 2-methylpropyl substituted

<400> SEQUENCE: 4

Phe Phe Arg Val His Leu Lys Arg Gly Gly Gly Gly Gly Gly Gly Gly

-continued

```
1           5              10             15
Gly Gly Gly Gly Gly Gly Gly Gly
            20
```